(«12») United States Patent
Mukhopadhyay et al.

(10) Patent No.: US 9,116,094 B1
(45) Date of Patent: *Aug. 25, 2015

(54) DETECTION OF ONE OR MORE INTERSTITIAL CONSTITUENTS IN A POLYCRYSTALLINE DIAMOND ELEMENT USING RADIATION

(71) Applicant: US SYNTHETIC CORPORATION, Orem, UT (US)

(72) Inventors: Debkumar Mukhopadhyay, Sandy, UT (US); Kenneth E. Bertagnolli, Riverton, UT (US)

(73) Assignee: US SYNTHETIC CORPORATION, Orem, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/517,547

(22) Filed: Oct. 17, 2014

Related U.S. Application Data

(63) Continuation of application No. 13/267,026, filed on Oct. 6, 2011, now Pat. No. 8,888,879.

(60) Provisional application No. 61/394,826, filed on Oct. 20, 2010.

(51) Int. Cl.
*B24D 3/00* (2006.01)
*B24D 3/02* (2006.01)
*B24D 11/00* (2006.01)
*B24D 18/00* (2006.01)
*C09K 3/14* (2006.01)
*C09C 1/68* (2006.01)
*G01N 23/00* (2006.01)
(Continued)

(52) U.S. Cl.
CPC .......... *G01N 23/005* (2013.01); *B24D 18/0009* (2013.01); *G01N 33/385* (2013.01); *G01N 33/40* (2013.01)

(58) Field of Classification Search
USPC .................................. 51/309, 293, 307, 308
See application file for complete search history.

(56) References Cited

U.S. PATENT DOCUMENTS

| | | | |
|---|---|---|---|
| 4,004,972 | A | 1/1977 | Mogard |
| 4,134,016 | A | 1/1979 | Larsen |
| 4,268,276 | A | 5/1981 | Bovenkerk |

(Continued)

OTHER PUBLICATIONS

U.S. Appl. No. 61/394,826, filed Oct. 20, 2010, Mukhopadhyay et al.

(Continued)

*Primary Examiner* — James McDonough
(74) *Attorney, Agent, or Firm* — Dorsey & Whitney LLP (57) ABSTRACT

In an embodiment, a method of non-destructively testing a polycrystalline diamond ("PCD") element includes providing a PCD element including a plurality of bonded diamond grains defining a plurality of interstitial regions, at least a portion of the plurality of interstitial regions including one or more interstitial constituents disposed therein. The method further includes exposing the PCD element to neutron radiation from a neutron radiation source, receiving a portion of the neutron radiation that passes through the PCD element, and determining at least one characteristic of the PCD element at least partially based on the portion of the neutron radiation received. For example, the at least one characteristic may be the presence and distribution of metal-solvent catalyst, residual metal-solvent catalyst, an infiltrant, residual infiltrant, or other interstitial constituents within a PCD element.

23 Claims, 6 Drawing Sheets

(51) Int. Cl.
*G01N 33/38* (2006.01)
*G01N 33/40* (2006.01)

(56) References Cited

U.S. PATENT DOCUMENTS

| | | | |
|---|---|---|---|
| 4,410,054 A | 10/1983 | Nagel et al. | |
| 4,468,138 A | 8/1984 | Nagel | |
| 4,506,327 A | 3/1985 | Tam | |
| 4,560,014 A | 12/1985 | Geczy | |
| 4,587,555 A | 5/1986 | Carollo et al. | |
| 4,604,649 A | 8/1986 | Carollo et al. | |
| 4,738,322 A | 4/1988 | Hall et al. | |
| 4,761,558 A | 8/1988 | Schulz | |
| 4,810,447 A | 3/1989 | Csillag | |
| 4,811,801 A | 3/1989 | Salesky et al. | |
| 4,832,708 A | 5/1989 | Csillag | |
| 4,913,247 A | 4/1990 | Jones | |
| 5,016,718 A | 5/1991 | Tandberg | |
| 5,028,789 A | 7/1991 | Whittemore | |
| 5,092,687 A | 3/1992 | Hall | |
| 5,120,327 A | 6/1992 | Dennis | |
| 5,135,061 A | 8/1992 | Newton, Jr. | |
| 5,154,245 A | 10/1992 | Waldenstrom et al. | |
| 5,219,720 A | 6/1993 | Black et al. | |
| 5,242,007 A | 9/1993 | Remmers et al. | |
| 5,296,712 A | 3/1994 | Swanson | |
| 5,334,495 A | 8/1994 | Black et al. | |
| 5,364,192 A | 11/1994 | Damm et al. | |
| 5,368,398 A | 11/1994 | Damm et al. | |
| 5,410,156 A | 4/1995 | Miller | |
| 5,413,695 A | 5/1995 | Miller | |
| 5,441,914 A | 8/1995 | Taft et al. | |
| 5,460,233 A | 10/1995 | Meany et al. | |
| 5,480,233 A | 1/1996 | Cunningham | |
| 5,544,713 A | 8/1996 | Dennis | |
| 5,553,105 A | 9/1996 | Xiao | |
| 5,688,486 A | 11/1997 | Watson et al. | |
| 5,753,426 A | 5/1998 | Nair et al. | |
| 5,778,963 A | 7/1998 | Parille et al. | |
| 5,796,110 A | 8/1998 | An et al. | |
| RE36,201 E | 4/1999 | Miller | |
| 5,977,007 A | 11/1999 | Lassow et al. | |
| 6,001,550 A | 12/1999 | Yacobucci et al. | |
| 6,011,296 A | 1/2000 | Hassard et al. | |
| 6,102,099 A | 8/2000 | Sturgis et al. | |
| 6,236,097 B1 | 5/2001 | Hassard et al. | |
| 6,401,537 B1 | 6/2002 | Gigliotti, Jr. et al. | |
| 6,544,308 B2 | 4/2003 | Griffin et al. | |
| 6,545,281 B1 | 4/2003 | McGregor et al. | |
| 6,619,368 B1 | 9/2003 | Springgate et al. | |
| 6,693,281 B2 | 2/2004 | Chen et al. | |
| 6,753,051 B1 | 6/2004 | Landry-Coltrain et al. | |
| 6,793,681 B1 | 9/2004 | Pope et al. | |
| 6,838,165 B2 | 1/2005 | Majumdar et al. | |
| 6,872,501 B2 | 3/2005 | Majumdar et al. | |
| 7,164,138 B2 | 1/2007 | McGregor et al. | |
| 7,214,943 B2 | 5/2007 | Katagiri et al. | |
| 7,238,203 B2 | 7/2007 | Bagga et al. | |
| 7,326,933 B2 | 2/2008 | Katagiri et al. | |
| 7,381,962 B2 * | 6/2008 | Goldberg | 250/370.09 |
| 7,473,287 B2 | 1/2009 | Belnap et al. | |
| 7,616,734 B1 * | 11/2009 | Corbett et al. | 378/46 |
| 7,918,293 B1 * | 4/2011 | Vail | 175/434 |
| 8,888,879 B1 * | 11/2014 | Mukhopadhyay et al. | 51/309 |
| 2002/0121604 A1 | 9/2002 | Katagiri | |
| 2002/0171042 A1 | 11/2002 | Chen et al. | |
| 2003/0036479 A1 | 2/2003 | Majumdar et al. | |
| 2003/0059602 A1 | 3/2003 | Majumdar et al. | |
| 2003/0073577 A1 | 4/2003 | Majumdar et al. | |
| 2003/0125739 A1 | 7/2003 | Bagga et al. | |
| 2003/0130484 A1 | 7/2003 | Gordon et al. | |
| 2003/0136540 A1 | 7/2003 | Springgate et al. | |
| 2003/0138608 A1 | 7/2003 | Landry-Coltrain et al. | |
| 2003/0148073 A1 | 8/2003 | Landry-Coltrain et al. | |
| 2003/0150294 A1 | 8/2003 | Stefansson et al. | |
| 2003/0165213 A1 | 9/2003 | Maglich | |
| 2003/0205359 A1 | 11/2003 | Springgate et al. | |
| 2004/0057926 A1 | 3/2004 | Ochoa et al. | |
| 2004/0159801 A1 | 8/2004 | Kishinami et al. | |
| 2004/0170934 A1 | 9/2004 | Majumdar et al. | |
| 2004/0188629 A1 | 9/2004 | Katagiri | |
| 2004/0210289 A1 | 10/2004 | Wang et al. | |
| 2004/0254419 A1 | 12/2004 | Wang et al. | |
| 2005/0025797 A1 | 2/2005 | Wang et al. | |
| 2005/0045827 A1 | 3/2005 | Katagiri et al. | |
| 2005/0079132 A1 | 4/2005 | Want et al. | |
| 2005/0107870 A1 | 5/2005 | Wang et al. | |
| 2005/0149173 A1 | 7/2005 | Hunter et al. | |
| 2005/0149175 A1 | 7/2005 | Hunter et al. | |
| 2005/0154445 A1 | 7/2005 | Hunter et al. | |
| 2005/0154453 A1 | 7/2005 | Hunter et al. | |
| 2005/0154454 A1 | 7/2005 | Hunter et al. | |
| 2005/0165467 A1 | 7/2005 | Hunter et al. | |
| 2005/0175661 A1 | 8/2005 | Hunter et al. | |
| 2005/0175662 A1 | 8/2005 | Hunter et al. | |
| 2005/0177103 A1 | 8/2005 | Hunter et al. | |
| 2005/0181004 A1 | 8/2005 | Hunter et al. | |
| 2005/0186242 A1 | 8/2005 | Hunter et al. | |
| 2005/0186243 A1 | 8/2005 | Hunter et al. | |
| 2005/0236577 A1 | 10/2005 | Katagiri | |
| 2005/0258372 A1 | 11/2005 | McGregor et al. | |
| 2005/0260160 A1 | 11/2005 | Huizinga et al. | |
| 2006/0023828 A1 | 2/2006 | McGregor et al. | |
| 2006/0024053 A1 | 2/2006 | Grant | |
| 2006/0043308 A1 | 3/2006 | McGregor et al. | |
| 2006/0056573 A1 | 3/2006 | McGregor et al. | |
| 2006/0149230 A1 | 7/2006 | Kwak et al. | |
| 2006/0246438 A1 | 11/2006 | McCall et al. | |
| 2006/0289814 A1 | 12/2006 | Kato | |
| 2006/0291606 A1 | 12/2006 | McGregor et al. | |
| 2007/0010702 A1 | 1/2007 | Wang et al. | |
| 2007/0017160 A1 | 1/2007 | Caldwell et al. | |
| 2007/0018110 A1 | 1/2007 | McGregor et al. | |
| 2007/0102646 A1 | 5/2007 | Goldberg | |
| 2007/0278413 A1 | 12/2007 | Katagiri et al. | |
| 2007/0293948 A1 | 12/2007 | Bagga et al. | |
| 2008/0175885 A1 | 7/2008 | Asgari | |
| 2008/0177378 A1 | 7/2008 | Asgari | |
| 2008/0195170 A1 | 8/2008 | Asgari | |
| 2008/0195189 A1 | 8/2008 | Asgari | |
| 2008/0195196 A1 | 8/2008 | Asgari | |
| 2008/0195198 A1 | 8/2008 | Asgari | |
| 2008/0200976 A1 | 8/2008 | Asgari | |
| 2008/0200995 A1 | 8/2008 | Sidebotham | |
| 2008/0213611 A1 | 9/2008 | Asgari | |
| 2008/0249637 A1 | 10/2008 | Asgari | |
| 2008/0249638 A1 | 10/2008 | Asgari | |
| 2008/0300637 A1 | 12/2008 | Austin et al. | |
| 2009/0117334 A1 | 5/2009 | Sogard et al. | |
| 2009/0192592 A1 | 7/2009 | Asgari | |
| 2009/0254182 A1 | 10/2009 | Kovarik et al. | |
| 2009/0302231 A1 | 12/2009 | McGregor et al. | |
| 2010/0143758 A1 | 6/2010 | Kim et al. | |

OTHER PUBLICATIONS

U.S. Appl. No. 13/267,026, filed Oct. 6, 2011, Mukhopadhyay et al.
Imaging with Neutrons: The Other Penetrating Radiation Glen MacGillivray, Nray Services Inc., Canada, available at least as early as Jul. 2010.
Neutron Imaging, At the spallation source SINQ Paul Scherrer Institut (PSI), Villigen PSI, Jul. 2006.
U.S. Appl. No. 13/267,026, Sep. 20, 2013, Office Action.
U.S. Appl. No. 13/267,026, Nov. 6, 2013, Office Action.
U.S. Appl. No. 13/267,026, Apr. 8, 2014, Office Action.
U.S. Appl. No. 13/267,026, Jul. 17, 2014, Notice of Allowance.
U.S. Appl. No. 13/267,026, Sep. 29, 2014, Notice of Allowance.
U.S. Appl. No. 13/267,026, Oct. 29, 2014, Issue Notification.

* cited by examiner

DETECTION OF ONE OR MORE INTERSTITIAL CONSTITUENTS IN A POLYCRYSTALLINE DIAMOND ELEMENT USING RADIATION

CROSS-REFERENCE TO RELATED APPLICATIONS

This application is a continuation of U.S. patent application Ser. No. 13/267,026 filed on 6 Oct. 2011, which claims priority of U.S. Provisional Application No. 61/394,826 filed on 20 Oct. 2010. Each of the foregoing applications is incorporated herein, in its entirety, by this reference.

BACKGROUND

Wear-resistant, polycrystalline diamond compacts ("PDCs") are employed in a variety of mechanical applications. For example, PDCs are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller-cone drill bits and fixed-cutter drill bits. A PDC cutting element typically includes a superabrasive diamond layer commonly known as a diamond table. The diamond table is formed and bonded to a cemented carbide substrate using a high-pressure/high-temperature ("HPHT") process. The PDC cutting element may be brazed directly into a preformed pocket, socket, or other receptacle formed in a bit body. The cemented carbide substrate may often be brazed or otherwise joined to an attachment member, such as a cylindrical backing. A rotary drill bit typically includes a number of PDC cutting elements affixed to the bit body. It is also known that a stud carrying the PDC may be used as a PDC cutting element when mounted to a bit body of a rotary drill bit by press-fitting, brazing, or otherwise securing the stud into a receptacle formed in the bit body.

Conventional PDCs are normally fabricated by placing a cemented tungsten carbide substrate into a container with a volume of diamond particles positioned on a surface of the cemented tungsten carbide substrate. A number of such containers may be loaded into an HPHT press. The substrate(s) and volume(s) of diamond particles are then processed under diamond-stable HPHT conditions. During the HPHT process, a metal-solvent catalyst cementing constituent of the cemented tungsten carbide substrate, such as cobalt from a cobalt-cemented tungsten carbide substrate, liquefies and infiltrates into interstitial regions between the diamond particles. The cobalt acts as a catalyst to promote intergrowth between the diamond particles, which results in formation of a polycrystalline diamond ("PCD") table of bonded diamond grains having diamond-to-diamond bonding therebetween that is bonded to the cemented tungsten carbide substrate. Interstitial regions between the bonded diamond grains are occupied by the metal-solvent catalyst.

Once formed, the PCD table may be leached so as to remove at least a portion of the cobalt or other metal-solvent catalyst, as the continued presence of such metal-solvent catalyst within the working surfaces of the PCD table can greatly decrease performance characteristics of the PCD table. For example, the wear resistance and thermal stability of a PCD table may be adversely affected by the presence of cobalt.

In order to accurately predict the quality and performance of PDCs, manufacturers and users of PDCs continue to seek improved non-destructive testing methods for testing PDCs.

SUMMARY

Embodiments of the invention relate to non-destructive testing methods for determining at least one characteristic of a PCD element, such as a PCD table of a PDC for use on a rotary drill bit. For example, the at least one characteristic may be the presence and distribution of metal-solvent catalyst, residual metal-solvent catalyst, an infiltrant, residual infiltrant, or other interstitial constituents within a PCD element. In an embodiment, a method of non-destructively testing a PCD element includes providing a PCD element including a plurality of bonded diamond grains defining a plurality of interstitial regions, with at least a portion of the plurality of interstitial regions including one or more interstitial constituents disposed therein. The method further includes exposing the PCD element to neutron radiation from a neutron radiation source, receiving a portion of the neutron radiation that passes through the PCD element, and determining at least one characteristic of the PCD element at least partially based on the portion of the neutron radiation received.

The use of neutron radiographic imaging may enable non-destructive testing of the manufactured product at significantly better resolution compared to alternative (e.g., X-ray) non-destructive imaging techniques. Furthermore, neutron radiographic imaging provides information relative to the presence and distribution of metal-solvent catalyst used to catalyze formation of the PCD element, residual metal-solvent catalyst remaining after subjecting the PCD element to a leaching process, infiltrant that infiltrates an at least partially leached PCD element during re-attachment to a substrate, or residual infiltrant remaining after subjecting a re-attached and infiltrated PCD element to a leaching process. In addition to providing greater resolution with respect to the presence and distribution of any residual metal-solvent catalyst or infiltrant, neutron radiographic imaging also enables detection of relatively light chemical elements and/or molecules (e.g., contaminants) such as hydrogen, oxygen, nitrogen, water, and other chemicals such as salts and oxides, which is an example of another interstitial constituent that may be detected by the inventive methods disclosed herein. Such elements and/or molecules may be introduced to the PCD element as by-products of the leaching process used to deplete metal-solvent catalyst and/or infiltrant from the PCD element.

Other embodiments include applications utilizing the non-destructively tested PCD elements and PDCs in various articles and apparatuses, such as rotary drill bits, machining equipment, and other articles and apparatuses.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical elements or features in different views or embodiments shown in the drawings.

DETAILED DESCRIPTION

I. Introduction

Embodiments of the invention relate to non-destructive testing methods for evaluating the quality of manufactured PCD elements (e.g., a PCD table of a PDC) in which at least a portion of the PCD element is exposed to neutron radiation from a neutron radiation source, a portion of the neutron radiation that passes through the PCD element is received, and at least one characteristic of the PCD element is determined based at least partially on the portion of the neutron radiation received. For example, such testing may reveal the presence and distribution of metal-solvent catalyst, an infiltrant, residual metal-solvent catalyst, residual infiltrant, one or more light chemical elements, one or more light chemical molecules, other interstitial constituents (e.g., salts and/or oxides), or combinations thereof (collectively referred to herein as interstitial constituents) within the interstitial regions of the PCD table. Such methods are particularly beneficial in evaluating at least that portion of the PCD table that is adjacent to exterior working surfaces of the PCD table that have been at least partially leached.

II. PCD Elements and PDCs

Figure 1A:
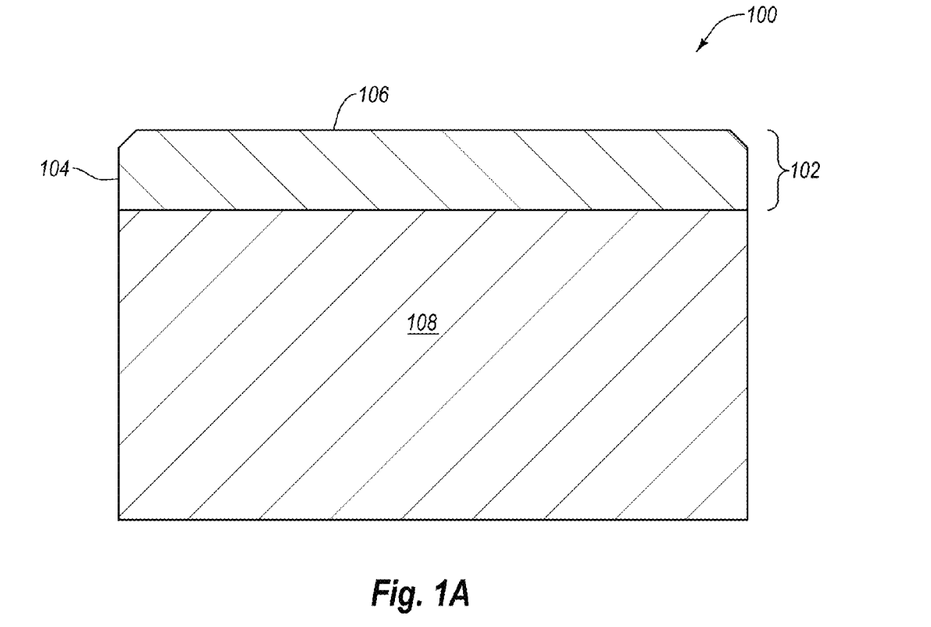
FIG. 1A is a cross-sectional view of an embodiment of a PDC, the PDC including a PCD table attached to a cemented carbide substrate.
Figure 1B:
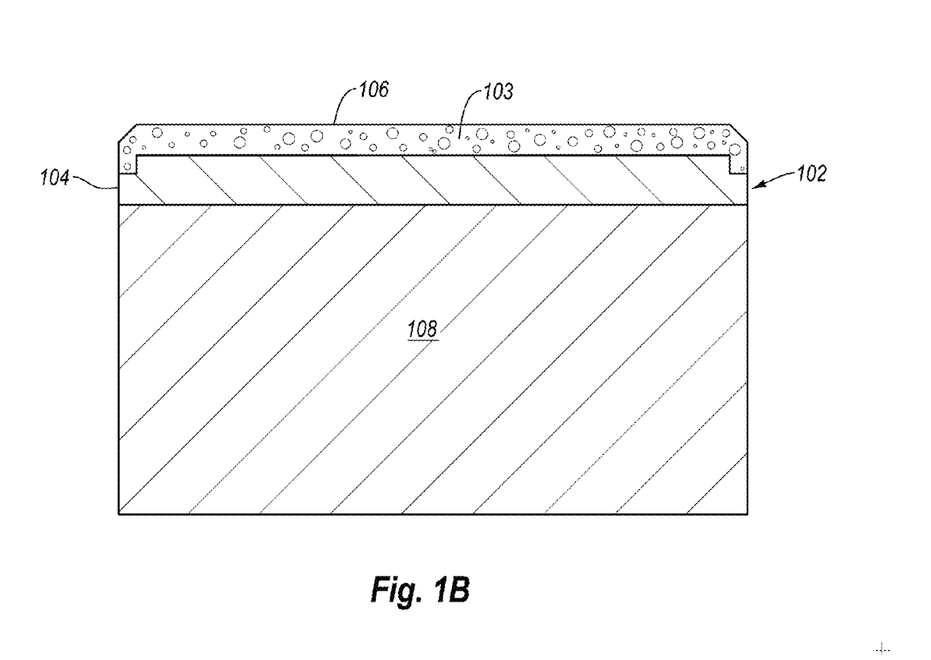
FIG. 1B is a cross-sectional view of an embodiment of a PDC including a leached PCD table.

FIG. 1A is a cross-sectional view of an embodiment of a PDC 100 including a PCD table 102 attached to a substrate 108. The PCD table 102 may be formed integral with or separately from the substrate 108. When formed separately, the PCD table 102 may be subsequently attached to the substrate 108. When the PCD table 102 is formed separate from the substrate 108 and subsequently attached to the substrate 108, an infiltrant (e.g., cobalt) from the substrate 108 may infiltrate into the PCD table 102 during an HPHT process in which the PCD table 102 becomes metallurgically bonded to substrate 108. Referring to FIG. 1B, in any case, the PCD table 102 may be at least partially leached (e.g., with a suitable acid) so as to remove some or all of the metal-solvent catalyst or infiltrant residing within the interstitial regions to form a leached region 103. The leaching may be performed to a PCD table that is attached to a cemented carbide substrate 108 or a PCD table that is separate from any such substrate.

The PCD table 102 includes a plurality of directly bonded-together diamond grains exhibiting diamond-to-diamond bonding (e.g., sp$^3$ bonding) therebetween, which define a plurality of interstitial regions. The PCD table 102 includes at least one lateral surface 104 and an upper exterior working surface 106. It is noted that at least a portion of the at least one lateral surface 104 may also function as a working surface that contacts a subterranean formation during drilling operations. In some embodiments, a chamfer may extend between the lateral surface 104 and working surface 106.

In an embodiment, the substrate 108 comprises a plurality of tungsten carbide or other carbide grains (e.g., tantalum carbide, vanadium carbide, niobium carbide, chromium carbide, and/or titanium carbide) cemented together with a metallic cementing constituent, such as cobalt, iron, nickel, or alloys thereof. For example, in an embodiment, the substrate 108 may be a cobalt-cemented tungsten carbide substrate. In some embodiments, the substrate 108 may include two or more different carbides (e.g., tungsten carbide and titanium carbide).

In an embodiment, the PCD table 102 is formed while simultaneously being metallurgically bonded with substrate 108. For example, a plurality of diamond particles may be positioned on an upper surface of the substrate 108, and the diamond particles and the substrate 108 may be placed in a pressure transmitting medium, such as a refractory metal can embedded in pyrophyllite or other pressure transmitting medium. The pressure transmitting medium, including the substrate 108 and diamond particles therein may be subjected to an HPHT process using an ultra-high pressure press to create temperature and pressure conditions at which diamond is stable. The temperature of the HPHT process may be at least about 1000° C. (e.g., about 1200° C. to about 1600° C.) and the pressure of the HPHT process may be at least 4.0 GPa (e.g., about 5.0 GPa to about 10.0 GPa) for a time sufficient to sinter the diamond particles to form the PCD table 102. For example, the pressure of the HPHT process may be about 5 GPa to about 7 GPa and the temperature of the HPHT process may be about 1150° C. to about 1450° C. (e.g., about 1200° C. to about 1400° C.).

During the HPHT process, the cementing constituent from the substrate 108 may be liquefied and may infiltrate into the diamond particles. The infiltrated cementing constituent functions as a metal-solvent catalyst that catalyzes formation of directly bonded-together diamond grains to form the PCD table 102. In embodiments in which the diamond particles were sintered previously, the metal-solvent cementing constituent simply infiltrates into the interstitial regions between adjacent diamond grains of the PCD table, resulting in a metallurgical bond between the PCD table 102 and the substrate 108.

As an alternative to providing the substrate 108 during sintering of the diamond particles, the PCD table 102 may be formed by placing the diamond particles along with a metal-solvent catalyst (e.g., cobalt powder and/or a cobalt disc) in a pressure transmitting medium, such as a refractory metal can embedded in pyrophyllite or other gasket medium. The pressure transmitting medium, including the diamond particles and metal-solvent catalyst therein, may be subjected to an HPHT process using an ultra-high pressure press to create temperature and pressure conditions at which diamond is stable. Such a process will result in the metal-solvent catalyst catalyzing direct bonding between diamond grains. At completion of the process, the metal-solvent catalyst resides within interstitial regions between the diamond grains, resulting in formation of a PCD table 102 separate from any cemented carbide substrate 108.

Even when the PCD table 102 is formed on the substrate 108, the PCD table 102 may be singulated to be freestanding by removing the substrate 108 using a suitable material removal process, such as grinding, electro-discharge machining, or combinations thereof. The freestanding PCD table may be leached to substantially remove all of the metal-solvent catalyst therefrom, and attached to a substrate (e.g., a cobalt-cemented tungsten carbide substrate) in a subsequent HPHT process so that an infiltrant from the substrate (e.g., cobalt from a cobalt-cemented tungsten carbide substrate) at least partially re-infiltrates the PCD table.

Removal of the metal-solvent catalyst or infiltrant from the PCD table that is freestanding or bonded to a substrate is beneficial as it increases the wear resistance and/or thermal stability the PCD table 102. For this reason, substantially all of the metal-solvent catalyst of a PCD table (e.g., adjacent to the working surface 106 and lateral surface 104) may subsequently be depleted of the metal-solvent catalyst or infiltrant via a leaching process by exposure to a suitable acid (e.g., aqua regia, nitric acid, hydrofluoric acid, or other suitable acid), and attached to a substrate 108 and infiltrated with an infiltrant from the substrate 108. For example, at least a portion of the PCD table may be immersed in the acid for about 2 to about 7 days (e.g., about 3, 5, or 7 days) or for a few weeks (e.g., about 2 to about 4 weeks) depending on the process employed. The leaching time and completeness of the metal-solvent catalyst or infiltrant removal depends on the porosity of the PCD table, among other factors. For example, decreased porosity exponentially decreases the completeness of depletion and/or requires additional leaching time.

Substantially all of the metal-solvent catalyst or infiltrant of the PCD table 102 that is bonded to the substrate 108 (e.g., adjacent to the working surface 106 and lateral surface 104) may also subsequently be depleted of the metal-solvent catalyst or infiltrant via a leaching process by exposure to any of the previously mentioned acids. For example, the leaching process may remove substantially all of the metal-solvent catalyst or infiltrant to a selected depth from the working surface 106 of about 50 μm to about 1000 μm (e.g., about 200 μm to about 500 μm) after a period of about 2 to about 4 weeks. Typically, leaching may not remove all of the metal-solvent catalyst or infiltrant within the leached region. For example, it is typical for the average concentration of residual metal-solvent catalyst or infiltrant to be about 0.5% to about 2% by weight, more typically 0.9% to about 1% by weight after leaching within the leached region. The residual metal-solvent catalyst or infiltrant may be measured, for example, by energy dispersive spectroscopy or magnetic saturation measurements.

III. Structure of Metal-Solvent Catalyst or Infiltrant Clusters

It is believed that even though the average concentration of the metal-solvent catalyst or infiltrant within the leached portion of the PCD table 102 is thus relatively low (e.g., no more than about 2% by weight), the distribution of residual metal-solvent catalyst or infiltrant within the leached portion may not be substantially uniform. In other words, the residual metal-solvent catalyst or infiltrant may be present as clusters including a plurality of portions in which the clusters of metal-solvent catalyst or infiltrant may be surrounded by diamond grains and interstitial regions containing little or no metal-solvent catalyst or infiltrant portions. Although the average concentration of metal-solvent catalyst or infiltrant may thus be relatively low (e.g., no more than about 2% by weight) within the leached region overall, there may be subregions within the leached region in which the presence of one or more clusters results in a concentration of metal-solvent catalyst or infiltrant that is significantly higher within the subregion.

Although not entirely understood, such clusters may remain even after leaching as a result of lower porosity in the subregion where the clusters remain and/or limited circulation in the acid leaching bath used to deplete the metal-solvent catalyst or infiltrant from the PCD table. Because the degree of completeness of metal-solvent catalyst or infiltrant removal depends exponentially on porosity, even a relatively moderate decrease in porosity within such a subregion may result in the continued presence of one or more clusters of metal-solvent catalyst or infiltrant remaining even after leaching for a significant period of time (e.g., about 2 to about 4 weeks), and even after the average concentration of metal-solvent catalyst or infiltrant has dropped to no more than about 2% by weight.

The presence of such clusters not only results in decreased wear resistance and/or thermal stability within the subregion in which the cluster is located, but also may result in problems, such as delamination of the PCD table 102 from the substrate 108 and/or poor infiltration of the PCD table 102 when the PCD table 102 is preformed and joined to a substrate in a separate attachment process. Furthermore, the presence of other interstitial constituents such as by-products of the leaching process (e.g., light chemical elements and/or light molecules, salts, oxides, or combinations thereof) may become trapped within the leached region of PCD table 102. For example, the light chemical elements and/or light molecules may include hydrogen, oxygen, nitrogen, water, other contaminants (e.g., salts and/or oxides), or combinations of the foregoing. The presence of such contaminants may also be detrimental to the performance characteristics of the PCD table.

Figure 1C:
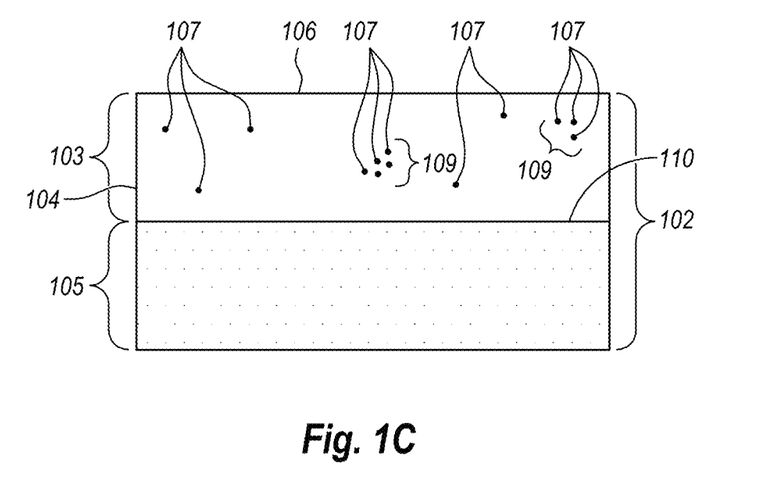
FIG. 1C is an enlarged schematic cross-sectional view of the PCD table of the PDC of FIG. 1A after a portion of the PCD table has been leached.

FIG. 1C shows an enlarged schematic cross-sectional view of the PCD table 102 including the leached region 103 shown in FIG. 1B adjacent to the working surface 106 and an un-leached region 105 below leached region 103 (e.g., adjacent to the substrate 108 (not shown)). Although the average concentration of metal-solvent catalyst or infiltrant 107 may be relatively low (e.g., no more than about 2% by weight) within leached region 103, the distribution of metal-solvent catalyst or infiltrant 107 may be non-uniform, including concentrated clusters 109 in which the atoms, particles, or other portions thereof are concentrated in close proximity to one another. Furthermore, other interstitial constituents, such as relatively light weight elements and/or molecules (e.g., having a molecular weight less than about 40), such as hydrogen, oxygen, nitrogen, water, or combinations thereof may be present within leached region 103 as by-products of the leaching process or as contaminants derived from other sources. Additionally, other interstitial constituents, such as salts and oxides (e.g., cobalt salts and oxides), may be present within leached region 103 as by-products of the leaching process or as contaminants derived from other sources. The presence of such contaminants may also be detrimental to the performance characteristics of PCD table 102 and/or the re-infiltration of an at least partially leached PCD table during a re-attachment to a substrate. Of course, such contaminants may also be present within un-leached region 105. In addition to detecting the presence of such interstitial constituents, the non-destructive testing may also show a location and configuration of an interface 110 between the leached region 103 and the un-leached region 105 of the PCD table 102.

Figure 1D:
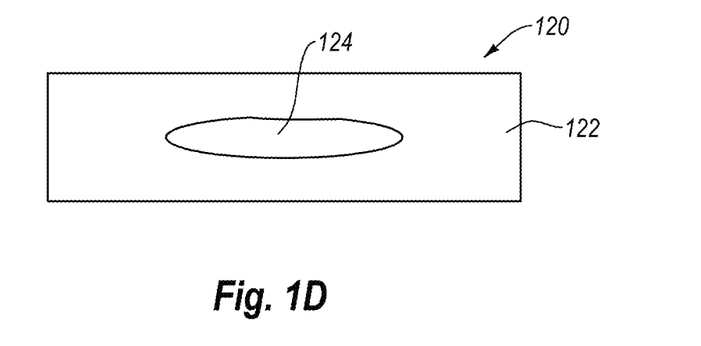
FIG. 1D is a schematic cross-sectional view of a partially leached PCD table having a leached region and an un-leached region formed by clusters.

FIG. 1D is a schematic cross-sectional view of a partially leached PCD table 120 having a leached region 122 and an un-leached region 124 formed by clusters having a different arrangement than shown in FIG. 1C. For example, the unleached region 124 may be generally centrally located in the partially leached PCD table 120 and defines a disk-like structure.

Figure 2A:
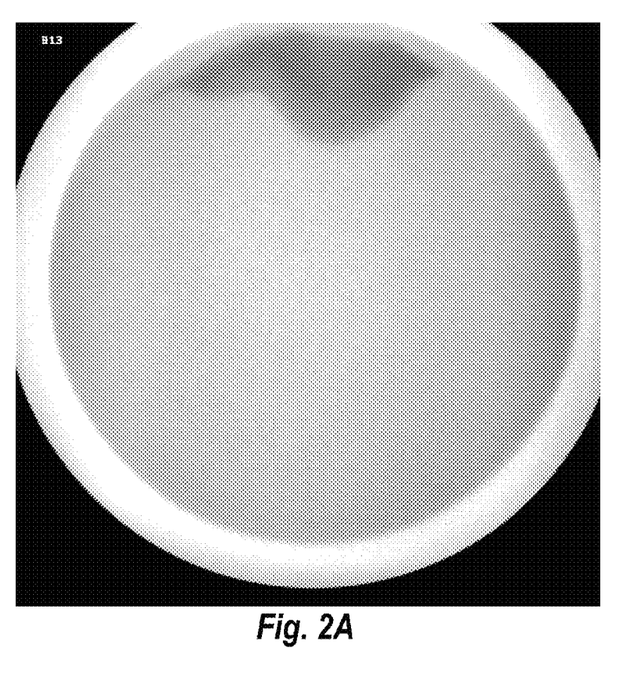
FIGS. 2A and 2B are radiographic images of a PCD table showing the presence of clusters of metal-solvent catalyst.
Figure 2B:
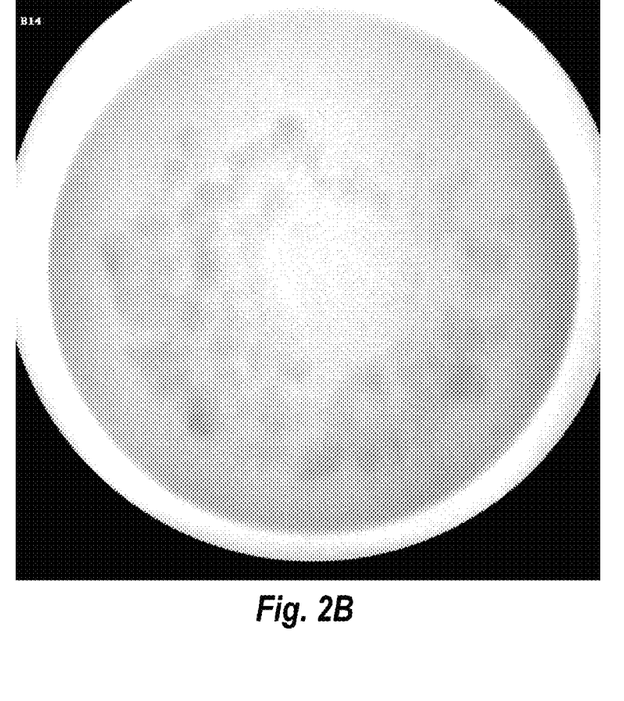

By way of example to merely illustrate the structure of clusters of metal-solvent catalyst, FIGS. 2A and 2B show images of PCD tables taken with x-ray radiography, which include clusters of metal-solvent catalyst disposed within at least a portion of the interstitial regions of the PCD table. The clusters are the darker regions in the images in FIGS. 2A and 2B. For example, a cluster that is shown in FIG. 2A may occur as a result of incomplete leaching (e.g., resulting from very low porosity). FIG. 2B shows a PCD table in which relatively smaller clusters are dispersed away from the center of the PCD table, in a pattern that is generally concentric relative to the "clean" center of the PCD table.

IV. Neutron Radiographic Non-Destructive Testing Methods

Figure 3:
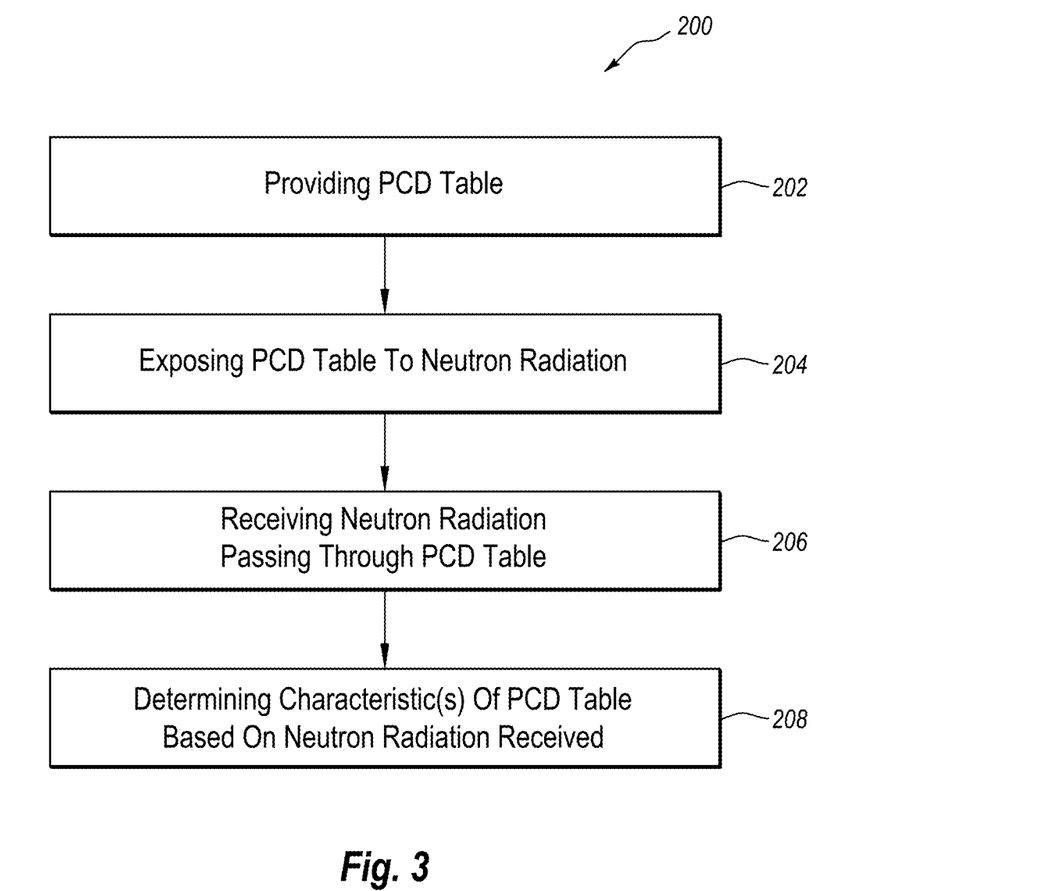
FIG. 3 is a flow chart of a non-destructive testing method according to an embodiment of the invention.

Any of the aforementioned PCD tables (whether freestanding or attached to a substrate) may be non-destructively tested using neutron radiographic imaging. FIG. 3 is a flow chart of a non-destructive testing method 200 according to an embodiment of the invention, which may be used to non-destructively test a PCD table. In act 202, a PCD table may be provided. The PCD table may be freestanding and leached or un-leached, or attached to a substrate and leached or un-leached. In order to detect the presence of anomalies within the PCD table 102, in act 204, the PCD table 102 may be exposed to neutron radiation (e.g., neutron beam) from a neutron radiation source. In act 206, a portion of the neutron radiation passes through the PCD table and is received by a detector (e.g., a radiation detector or photosentive film) so that an image of the PCD table showing the presence of interstitial constituents disposed within the interstitial regions between the diamond grains and the diamond grains is generated. In act 208, one or more characteristics of the PCD table may be determined at least partially based upon the portion of neutron radiation received.

The one or more characteristics of the PCD table determined may be the presence and distribution of metal-solvent catalyst in the PCD table, residual metal-solvent catalyst in the PCD table, an infiltrant in the PCD table, residual infiltrant in the PCD table, other interstitial constituents (e.g., light elements and/or molecules) within the PCD table, or combinations of the foregoing. As another example, when the PCD table is attached to a substrate (e.g., the PCD table 102 shown in FIG. 1B), the method 200 may be used to determine the location of the interface 110 (e.g., leach depth) and/or any of the other of the one or more characteristics.

Use of a neutron beam imaging technique can be advantageous over alternative testing and/or detection methods, as it is non-destructive, and provides for better resolution as compared to alternative radiation imaging techniques (e.g., X-ray and/or gamma ray). For example, with X-ray and gamma ray imaging, the detection of many light weight contaminants is not possible.

Any suitable neutron radiation source may be used. For example, cold neutron radiation sources, thermal neutron radiation sources, fast neutron radiation sources, or combinations thereof may be employed in the neutron beam imaging technique. By way of non-limiting example, cold neutron sources may exhibit energies of less than about 0.025 eV, thermal neutrons may exhibit energies of between about 0.025 eV and about 1 eV (e.g., perhaps most typically about 0.025 eV), and fast neutrons may exhibit energies of at least about 1 keV (e.g., even as high as 14 MeV or greater). Cold and/or thermal neutron sources may be particularly preferred in some embodiments, as they may exhibit greater contrast (as compared to fast neutrons) between different elements and/or molecules within the PCD table being examined. Although fast neutron sources may exhibit lower contrast, they may also have a greater ability to penetrate to a greater thickness.

Imaging with neutrons may involve production of images on film, digital production of images, or the production of three-dimensional data (tomography). The neutron flux for generating the neutron beam used in imaging may be produced from conventional sources, such as nuclear reactors (e.g., producing cold, thermal and/or fast neutrons), or deuteron-tritium tubes (i.e., D-T tubes) in which a deuteron beam impinges upon a tritiated target, which yields fast neutrons (e.g., 14 MeV neutrons). Such fast neutrons may be used directly for fast neutron imaging or may be moderated to a lower temperature to allow thermal or perhaps even cold neutron imaging. Accelerators for accelerating beams of protons or deuterons are another exemplary source of neutrons.

The manufacturing process and/or precursor materials used to fabricate the PCD elements (e.g., the PCD tables and/or PDCs) may be adjusted in response to the non-destructive neutron radiographic imaging via the method 200. For example, the HPHT process conditions (e.g., pressure, temperature, time, or combinations thereof), leaching acid composition, leaching time, diamond particle size, or combinations of the foregoing may be modified in view of the results of the non-destructive neutron radiographic imaging via the method 200.

In some cases, one or more samples of manufactured PCD tables may be sent to a third party for neutron imaging, or the testing may be done by the manufacturer, depending on the availability of the neutron source.

Figure 4:
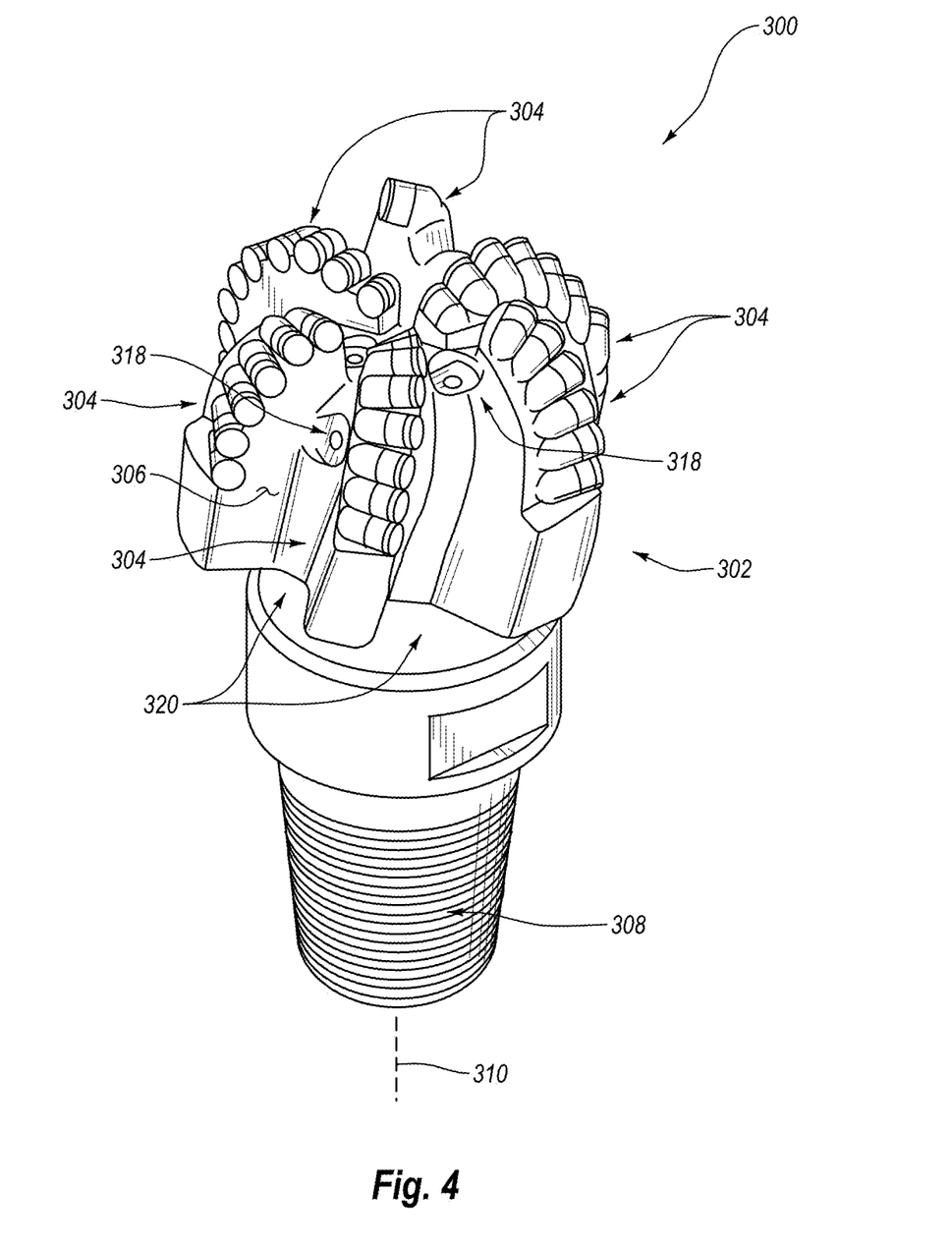
FIG. 4 is an isometric view of an embodiment of a rotary drill bit that may employ one or more of the PCD elements and/or PDCs non-destructively tested according to one or more embodiments of the invention.
Figure 5:
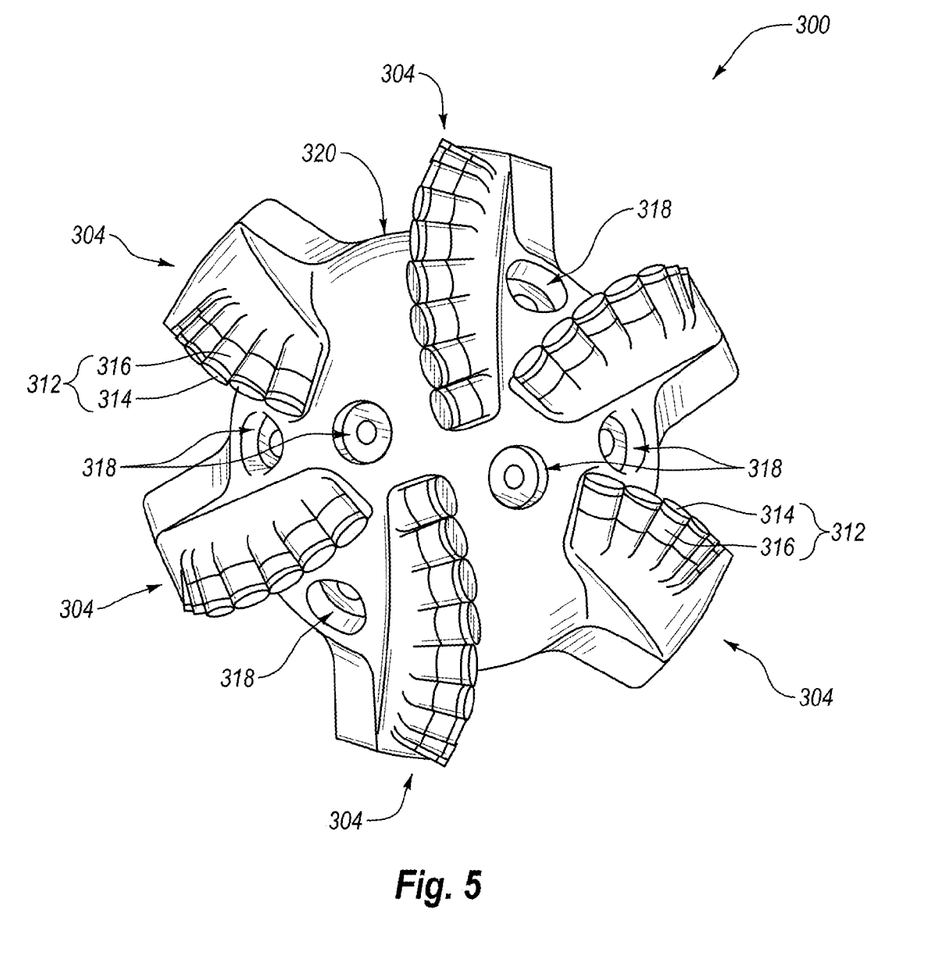
FIG. 5 is a top elevation view of the rotary drill bit shown in FIG. 4.

The non-destructively tested PCD elements and PDCs may be installed on a rotary drill bit. FIG. 4 is an isometric view and FIG. 5 is a top elevation view of an embodiment of a rotary drill bit 300 that includes at least one PDC configured according to any of the disclosed PDC embodiments. The rotary drill bit 300 comprises a bit body 302 that includes radially and longitudinally extending blades 304 having leading faces 306, and a threaded pin connection 308 for connecting the bit body 302 to a drilling string. The bit body 302 defines a leading end structure for drilling into a subterranean formation by rotation about a longitudinal axis 310 and application of weight-on-bit. At least one PDC element (e.g., a PDC), manufactured and/or non-destructively tested according to any of the previously described embodiments, may be affixed to the bit body 302. With reference to FIG. 5, each of a plurality of PDCs 312 is secured to the blades 304 of the bit body 302 (FIG. 4). For example, each PDC 312 may include a PCD table 314 bonded to a substrate 316. More generally, the PDCs 312 may comprise any PDC disclosed herein, without limitation, which is configured and non-destructively tested according to any of the previously described embodiments. Circumferentially adjacent blades 304 define so-called junk slots 320 therebetween. Additionally, the rotary drill bit 300 includes a plurality of nozzle cavities 318 for communicating drilling fluid from the interior of the rotary drill bit 300 to the PDCs 312.

FIGS. 4 and 5 merely depict one embodiment of a rotary drill bit that employs at least one PDC tested and structured in accordance with the disclosed embodiments, without limitation. The rotary drill bit 300 is used to represent any number of earth-boring tools or drilling tools, including, for example, core bits, roller-cone bits, fixed-cutter bits, eccentric bits, bi-center bits, reamers, reamer wings, or any other downhole tool including superabrasive compacts, without limitation.

The tested PCD elements disclosed herein (e.g., PDC 100 of FIG. 1A) may also be utilized in applications other than cutting technology. For example, the disclosed PDC embodiments may be used in wire dies, bearings, artificial joints, inserts, cutting elements, and heat sinks Thus, any of the PDCs and other PCD elements disclosed herein may be employed in an article of manufacture including at least one superabrasive element or compact.

Thus, the tested PCD element disclosed herein may be used in any apparatus or structure in which at least one conventional PCD element is typically used. In an embodiment, a rotor and a stator, assembled to form a thrust-bearing apparatus, may each include one or more PDCs (e.g., PDC 100 of FIG. 1A) configured according to any of the embodiments disclosed herein and may be operably assembled to a downhole drilling assembly. U.S. Pat. Nos. 4,410,054; 4,560,014; 5,364,192; 5,368,398; and 5,480,233, the disclosure of each of which is incorporated herein, in its entirety, by this reference, disclose subterranean drilling systems within which bearing apparatuses utilizing superabrasive compacts disclosed herein may be incorporated. The embodiments of PCD elements disclosed herein may also form all or part of heat sinks, wire dies, bearing elements, cutting elements, cutting inserts (e.g., on a roller-cone-type drill bit), machining inserts, or any other article of manufacture as known in the art. Other examples of articles of manufacture that may use any of the tested PDCs disclosed herein are disclosed in U.S. Pat. Nos. 4,811,801; 4,268,276; 4,468,138; 4,738,322; 4,913,247; 5,016,718; 5,092,687; 5,120,327; 5,135,061; 5,154,245; 5,460,233; 5,544,713; and 6,793,681, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, are open ended and shall have the same meaning as the word "comprising" and variants thereof (e.g., "comprise" and "comprises").

What is claimed is:

1. A method of non-destructively testing a polycrystalline diamond element, the method comprising:
    providing the polycrystalline diamond element including a plurality of bonded diamond grains defining a plurality of interstitial regions, at least a portion of the plurality of interstitial regions including one or more interstitial constituents therein;
    exposing the polycrystalline diamond element to radiation from a radiation source;
    receiving a portion of the radiation from the polycrystalline diamond element; and
    detecting at least one Group VIII metal and at least one chemical compound that does not include a Group VIII metal in the polycrystalline diamond element at least partially based on the portion of the radiation received.

2. The method of claim 1 wherein the polycrystalline diamond element is at least partially leached.

3. The method of claim 2 wherein detecting at least one Group VIII metal and at least one chemical compound that does not include a Group VIII metal at least partially based on the portion of the radiation received includes determining a location of an interface between a first region that extends inwardly from an exterior working surface of the at least partially leached polycrystalline diamond table and is substantially free of the at least one Group VIII metal and a second region of the at least partially leached polycrystalline diamond table that includes the at least one Group VIII metal.

4. The method of claim 2 wherein the one or more interstitial constituents include a one or more of at least one Group VIII metal, an infiltrant, a residual metal-solvent catalyst including a Group VIII metal, a residual infiltrant, one or more light chemical elements, one or more light chemical molecules, one or more salts, or one or more oxides.

5. The method of claim 2 wherein the at least partially leached polycrystalline diamond element is bonded to a substrate.

6. The method of claim 1 wherein detecting at least one Group VIII metal and at least one chemical compound that does not include a Group VIII metal in the polycrystalline diamond element at least partially based on the portion of the radiation received includes detecting at least one of a presence of clusters of the at least one Group VIII metal or the least one chemical compound that does not include a Group VIII metal disposed within a portion of the interstitial regions.

7. The method of claim 1 wherein detecting at least one Group VIII metal and at least one chemical compound that does not include a Group VIII metal in the polycrystalline diamond element at least partially based on the portion of the radiation received includes detecting a presence of one or more of light chemical elements or light chemical molecules within a portion of the interstitial regions.

8. The method of claim 7 wherein the one or more of light chemical elements or light chemical molecules include at least one of hydrogen, oxygen, nitrogen, or water.

9. The method of claim 1 wherein the radiation source includes a neutron radiation source, and wherein the radiation includes neutron radiation.

10. The method of claim 1 wherein the one or more interstitial constituents include one or more of at least one Group VIII metal, an infiltrant, one or more light chemical elements, one or more light chemical molecules, one or more salts, or one or more oxides.

11. The method of claim 1 wherein receiving a portion of the radiation from the polycrystalline diamond element includes receiving the portion of the radiation that passes through the polycrystalline diamond element.

12. The method of claim 1, further comprising modifying a manufacturing process used to fabricate the polycrystalline diamond element at least partially based on the detected at least one Group VIII metal or at least one chemical compound that does not include a Group VIII metal.

13. The method of claim 12 wherein modifying a manufacturing process used to fabricate the polycrystalline diamond element at least partially based on the detected at least one Group VIII metal or at least one chemical compound that does not include a Group VIII metal includes modifying at least one high-pressure/high-temperature process condition used to fabricate the polycrystalline diamond element.

14. The method of claim 12 wherein modifying a manufacturing process used to fabricate the polycrystalline diamond element at least partially based on the detected at least one Group VIII metal or at least one chemical compound that does not include a Group VIII metal includes modifying a leaching acid composition, leaching time, diamond particle size, or combinations thereof.

15. The method of claim 1, further comprising:
    correlating the detected presence of the at least one Group VIII metal or at least one chemical compound that does not include a Group VIII metal in the polycrystalline diamond element to at least one performance characteristic of the polycrystalline diamond element; and modifying a manufacturing process used to fabricate the polycrystalline diamond element at least partially based on the at least one performance characteristic.

16. A method of non-destructively testing a polycrystalline diamond element, the method comprising:

providing an at least partially leached polycrystalline diamond element including a plurality of bonded diamond grains defining a plurality of interstitial regions, at least a portion of the plurality of interstitial regions including one or more interstitial constituents disposed therein;

exposing the at least partially leached polycrystalline diamond element to radiation from a radiation source;

receiving a portion of the radiation that passes through the at least partially leached polycrystalline diamond element;

at least partially based on the portion of the radiation received, detecting at least one Group VIII metal and at least one chemical compound within a portion of the interstitial regions of the at least partially leached polycrystalline diamond element; and correlating the detected at least one Group VIII metal or at least one chemical compound that does not include a Group VIII metal within the portion of the interstitial regions of the at least partially leached polycrystalline diamond element with at least one performance characteristic of the at least partially leached polycrystalline diamond element.

17. The method of claim 16, further comprising modifying a manufacturing process used to fabricate the at least partially leached polycrystalline diamond element at least partially based on the at least one performance characteristic.

18. The method of claim 16 wherein detecting at least one Group VIII metal and at least one chemical compound that does not include a Group VIII metal within a portion of the interstitial regions of the at least partially leached polycrystalline diamond element includes detecting at least one leaching by-product within a portion of the interstitial regions of the at least partially leached polycrystalline diamond element.

19. The method of claim 16 wherein the at least one chemical compound includes at least one of hydrogen, oxygen, nitrogen, water, salts, or oxides.

20. A method of non-destructively testing a polycrystalline diamond element, the method comprising:

providing an un-leached polycrystalline diamond element including a plurality of bonded diamond grains defining a plurality of interstitial regions, at least a portion of the plurality of interstitial regions including one or more interstitial constituents disposed therein;

exposing the un-leached polycrystalline diamond element to radiation from a radiation source;

receiving a portion of the radiation that passes through the un-leached polycrystalline diamond element;

at least partially based on the portion of the radiation received, detecting at least one Group VIII metal and at least one chemical compound that does not include a Group VIII metal within a portion of the interstitial regions of the un-leached polycrystalline diamond element.

21. The method of claim 20, wherein the un-leached polycrystalline diamond element is bonded to a substrate.

22. The method of claim 20, further comprising correlating the detected at least one Group VIII metal or at least one chemical compound that does not include a Group VIII metal within the portion of the interstitial regions of the un-leached polycrystalline diamond element with at least one performance characteristic of the un-leached polycrystalline diamond element.

23. The method of claim 22, further comprising modifying a manufacturing process used to fabricate the un-leached polycrystalline diamond element at least partially based on the at least one performance characteristic.

* * * * *